United States Patent [19]

Stahl et al.

[11] Patent Number: 4,760,077
[45] Date of Patent: Jul. 26, 1988

[54] PYRROTHINE DERIVATIVES AND PHARMACEUTICAL USE THEREOF

[75] Inventors: Peter Stahl, Bernried; Hans Seidel, Tutzing; Herbert Von der Eltz, Weilheim; Otto-Henning Wilhelms, Weinheim-Rittenweier; Androniki Roesch, Mannheim 1, all of Fed. Rep. of Germany

[73] Assignee: Boehringer Mannheim GmbH, Mannheim, Fed. Rep. of Germany

[21] Appl. No.: 874,170

[22] PCT Filed: Sep. 19, 1985

[86] PCT No.: PCT/EP85/00489

§ 371 Date: May 15, 1986

§ 102(e) Date: May 15, 1986

[87] PCT Pub. No.: WO86/01716

PCT Pub. Date: Mar. 27, 1986

[30] Foreign Application Priority Data

Sep. 20, 1984 [DE] Fed. Rep. of Germany ....... 3434562

[51] Int. Cl.$^4$ ............... C07D 495/04; C07D 207/273; A61K 31/40; A61K 31/385
[52] U.S. Cl. .................................... 514/412; 514/425; 548/453; 548/544
[58] Field of Search ............... 548/453, 577; 514/412, 514/425

[56] References Cited

U.S. PATENT DOCUMENTS 2,689,854  9/1954  Tanner et al. .................. 548/453
2,752,359  6/1956  Celmer ........................... 548/453

OTHER PUBLICATIONS

Ninomiya et al., Chem. and Pharm. Bull., vol. 28, pp. 3157–3162, (1980).

Primary Examiner—Richard L. Raymond
Assistant Examiner—D. B. Springer
Attorney, Agent, or Firm—Felfe & Lynch

[57] ABSTRACT

There is described the use of pyrrothine derivatives of the general formula I

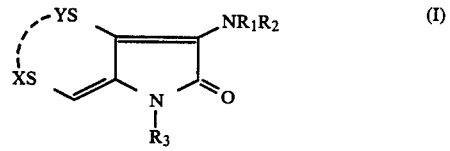

wherein $R_1$ and $R_3$ signify hydrogen or methyl, $R_2$ hydrogen, methyl or an acyl group with 1 to 5 carbon atoms and X and Y signify hydrogen, an equivalent of a physiolgically acceptable cation or together a single bond, for the inhibition of the allergen-induced degranulation of peripheral leukocytes.

10 Claims, No Drawings

PYRROTHINE DERIVATIVES AND PHARMACEUTICAL USE THEREOF

The present invention concerns the use of pyrrothine compounds for the inhibition of allergen-induced degranulation of peripheral leukocytes.

It is known that the derivatives of pyrrothine (4-methyl-6-amino-1,2-dithiolo[4,3-b]pyrrol-5(4H)-one, such as e.g. the N-acetyl derivative (thiolutin) or the N-propionyl derivative (aureothricin), obtained from Streptomyces culture filtrates, represent antibiotics with action against gram-positive and gram-negative bacteria, pathogenic fungi and protozoa (cf. W. D. Celmer and I. A. Solomons, J. Am. Chem. Soc. 77 (1955) 2861); the total synthesis of these antibiotics is described by U. Schmidt and F. Geiger (cf. Angew. Chemie 74 (1962) 328; Liebigs Ann. Chem. 664 (1963) 168).

Surprisingly, it has now been found that such pyrrothine derivatives also possess an outstanding anti-allergic action; they inhibit e.g. the human allergen-induced degranulation of peripheral leukocytes. The corresponding dimercapto compounds obtained by the reductive fission of the S—S bond of the pyrrothine derivatives also show a similar action.

Therefore, the subject of the present invention is the use of pyrrothine derivatives of the general formula I

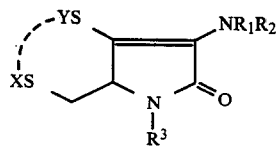

wherein $R_1$ and $R_3$ signify hydrogen or methyl, $R_2$ hydrogen, methyl or an acyl group with 1 to 5, especially 2 to 4 carbon atoms and X and Y hydrogen, an equivalent of a physiologically acceptable cation or together a single bond, for the inhibition of allergeninduced degranulation of peripheral leukocytes.

In preferred compounds of the formula I, $R_1$ and $R_2$ are different and especially $R_1$ hydrogen and $R_2$ methyl or acyl with 1 to 5, especially 2 to 4 carbon atoms. $R_3$ is preferably a methyl group.

For the use according to the invention for the combating of allergies, compounds of the formula Ia are preferred, i.e. thus the compounds of the formula I, in which X and Y together form a single bond,

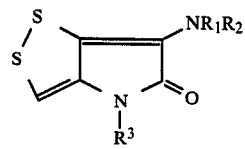

wherein $R_1$, $R_2$ and $R_3$ possess the above-given meaning.

The compounds of the formula I, in which X and Y together do not form a single bond but rather signify a hydrogen atom or an equivalent of a physiologically acceptable cation, are represented by the formula Ib:

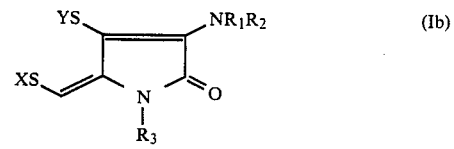

wherein $R_1$, $R_2$ and $R_3$ possess the above-given meanings. They are preferably present in the form of their salts (X,Y=equivalent of a physiologically acceptable cation).

The compounds of the formula I, wherein $R_1$, $R_2$ and $R_3$ signify methyl and X and Y hydrogen, an equivalent of a physiologically acceptable cation or together a single bond, are new compounds.

The compounds of the general formula Ib, for which hitherto a use as medicament is not known, show, in the case of the use according to the invention, the same anti-allergic effectiveness as the compounds of the formula Ia. Therefore, the subject of the present invention is also a pharmaceutical composition which contains a compound of the formula Ib, wherein X, Y, $R_1$, $R_2$ and $R_3$ possess the above-given meaning, or a new compound of the formula I, wherein $R_1$, $R_2$ and $R_3$ signify methyl and X and Y hydrogen, an equivalent of a physiologically acceptable cation or together a single bond. The pharmaceutical compositions can also contain two or more of the compounds of the formula I employed according to the invention.

An acyl group with 1 to 5 carbon atoms can be straight-chained or branched and is e.g. valeryl, isovaleryl and trimethylacetyl and especially butyryl, isobutyryl, propionyl, acetyl and formyl.

A physiologically acceptable cation X and Y can be mono- or polyvalent and is especially a mono- or divalent physiologically acceptable cation, such as e.g. $Ca^{2+}$, $Na^+$ or $K^+$; however, it can also signify ammonium or an organic ammonium cation, such as e.g. mono-, di- or trialkylammonium, whereby the alkyl group then especially signifies methyl.

The compounds of the formula Ia are known or can be prepared in per se known manner by synthetic ways or from Actinomycetales (cf. The Chemistry of Heterocyclic Compounds, Part 1, D. S. Breslow, H. Skolnik, Interscience Publishers, 1966, page 420; U. Schmidt and F. Geiger, Angew. Chemie 74 (1962) 328; Liebigs Ann. Chem. 664 (1963), 168).

The compounds of the formula Ib, in which X and Y signify a hydrogen atom, can be obtained from the corresponding compounds of the formula Ia in per se known manner by reductive ring fission with complex hydrides, especially with sodium borohydride (cf. U. Schmidt and F. Geiger, Liebigs Ann. Chem. 664 (1963), 168); these compounds can be converted in the usual way to their salts, in which X and Y represent a pharmaceutically acceptable cation, and are preferably used in the form of their salts, e.g. directly in the form or solution obtained by the reductive fission.

According to the invention, the compounds of the formula I are used individually or as mixture of two or more compounds. Therefore, there can also be used the active material mixture obtained from certain kinds of Actinomycetales (cf. e.g. W. D. Celmer, I. A. Solomons, J. Am. Chem. Soc. 77 (1955) 2861; U. Schmidt and F. Geiger, Angew. Chemie 74 (1962) 328). It has been found that an active material mixture, well suited from the viewpoint of the preparation (active material yield) and of the use according to the invention, can be expediently obtained from Streptoverticillium thioluteum (DSM No. 40027) and especially from its culture broth (culture filtrate). The working up can thereby take place in a way per se known for such processes, such as e.g. concentration and/or extraction of the culture broth. As main active material components of the culture filtrate of Streptoverticillium thioluteum were ascertained: about 70% aureothricin (M.W.=242, formula Ia: $R_1=H$, $R_2=$propionyl, $R_3=CH_3$); about 15% thiolutin (M.W. 228, formula Ia: $R_1=H$, $R_2=$acetyl, $R_3=CH_3$); about 10% isobutyrylpyrrothin (M.W.=256, formula Ia: $R_1=H$, $R_2=$isobutyryl, $R_3=CH_3$).

For the detection of the anti-allergic action, there was measured the inhibition of the allergen-induced degranulation reaction of peripheral leukocytes; one operated according to the method of R. P. Siraganian and W. A. Hook (Manual of Clinical Immunology, 2nd edition 1980, pub. N. R. Rose and H. Friedman, Am. Soc. for Microbiology, pages 808 to 821). As comparison substance, there was employed the known degranulation inhibitor theophylline.

In the following Table I are given the inhibition data $ID_{50}$ (mol/l. for 50% inhibition in vitro) and toxicities $LD_{50}$ (p.o., mg./kg. mouse; for the toxicity cf. also 118th Am. Chem. Soc. Meet., Chicago, Sept. 1950, Abstracts of Papers, page 18a; Seneca et al. Antibiol.+- Chemother. 2, 357 (1952); U.S. Pat. No. 2,798,811) of compounds used according to the invention and of the comparison substance theophylline.

TABLE I

| compound | $ID_{50}$ | $LD_{50}$ |
| --- | --- | --- |
| pyrrothine | $9 \times 10^{-7}$ | — |
| thiolutin | $4 \times 10^{-7}$ | 25 |
| aureothricin | $9 \times 10^{-7}$ | — |
| isobutyrylpyrrothine | $1.7 \times 10^{-6}$ | — |
| Ib, $R_1 = H$, $R_2 = COCH_3$, $R_3 = CH_3$, as Na salt | $2.5 \times 10^{-6}$ | — |
| Ia, $R_1$, $R_2$, $R_3 = CH_3$ | $4.6 \times 10^{-6}$ | — |
| Ib, $R_1$, $R_2$, $R_3 = CH_3$ as Na salt | $5.0 \times 10^{-6}$ | — |
| theophylline | $5 \times 10^{-3}$ | 540 |

From the values of Table I, there is calculated for thiolutin a therapeutic index $LD_{50}/ID_{50}$ of $6.2 \times 10^7$, for the comparison compound theophylline one of $0.8 \times 10^3$; thus, the compound used according to the invention possesses a substantially higher factor (of more than $10^4$!), which demonstrates the greater pharmaceutical breadth and the good suitability of the compounds used according to the invention bound up therewith.

The compounds of the formula I used according to the invention can be used in the pharmaceutical compositions and forms of administration especially suitable for anti-allergics, e.g. as tablets, dragees, suppositories, injection solutions, syrups, inhalation sprays etc. The medicaments contain the active material, preferably together with usual pharmaceutical carrier and dilution agents, optionally also in combination with other active materials, such as e.g. further anti-allergics, or further suitable active materials for allergy therapy, such as e.g. fever-reducing agents, anti-inflammatory-acting agents, vitamins etc. The daily administration dose depends especially upon the nature and severity of the illness; in the case of adult humans, it amounts, as a rule, to 0.1 to 10 mg. active substances.

EXAMPLES

EXAMPLE 1

Culture of Streptoverticillium thioluteum DSM 40027

Composition of the culture medium:

| | |
| --- | --- |
| starch (separately heated) | 20 g. |
| peptone from meat, tryptic-digested (Merck) | 5 g. |
| yeast extract (Difco) | 4 g. |
| $CaCO_3$, precipitated | 2 g. |
| $KNO_3$ | 1 g. |
| $K_2HPO_4$ | 0.5 g. |
| $MgSO_4.7H_2O$ | 1 g. |
| NaCl | 0.5 g. |
| $FeSO_4 \times 7\ H_2O$ | 0.02 g. | dissolved in 1 l. tap water, pH about 7.0.

High synthesis capacities are achieved in this medium under standard fermentation conditions (fermentation period 25 to 56 hours), with good growth.

For the isolation of an active material mixture, the culture filtrate is obtained by centrifuging.

EXAMPLE 2

Isolation of pure active materials from Streptoverticillium thioluteum DSM 40027.

The culture filtrate obtained according to Example 1 (20 l., pH=6) was concentrated to 2 l. and extracted with ethyl acetate. The organic phase was evaporated and possibly chromatographed with silica gel/chloroform; as residue, there remains a strongly yellow coloured powder; after recrystallisaton from acetone, heterogeneous crystals are obtained (about 0.4 g.). For the separation of the mixture, the crystals are subjected to a further chromatography on silica gel (methylene chloride→methylene chloride/acetone=8/2). There were eluted the fractions 1 (about 35 mg.), 2 (about 165 mg.), the mixed fractions ½ (about 45 mg.) and the fraction 3 (about 55 mg.). The fractions correspond to the following known compounds: 1=isobutyrylpyrrothin, 2=aureothricin, 3=thiolutin.

EXAMPLE 3

3-Acetamido-4-mercapto-5-mercaptomethylene-1-methylpyrrolin-2-one disodium salt of the structural formula

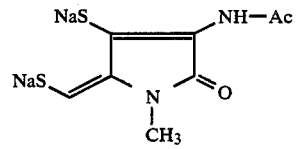

Thiolutin reduction:

228 mg. (1 mmol) Thiolutin are suspended in 100 ml. water and mixed with 76 mg. (2 mmol) $NaBH_4$. One stirs at room temperature until a clear solution is formed. The product can be purified chromatographically (silica gel) under a nitrogen atmosphere.

$R_F=0.58$, $CHCl_3/CH_3OH$ 1/1

$ID_{50}=2.5 \times 10^{-6}$

EXAMPLE 4

N,N-Dimethylpyrrothine of the structural formula

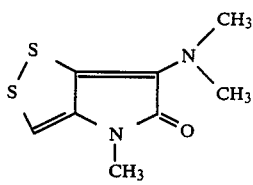

1.14 g. (5 mmol) Thiolutin are saponified according to the instructions of CELMER and SOLOMONS J. Am. Chem. Soc. 77 (1955) 2861 to phyrrothine hydrochloride and converted into the free base with excess ammonia. This is taken up in 10 ml. acetonitrile and 5 ml. formalin and mixed with 0.95 g. NaCNBH$_3$. While stirring, one adds 0.5 ml. glacial acetic acid dropwise thereto over the course of 30 minutes, stirs for 2 hours at room temperature and adds a further 0.5 ml. glacial acetic acid thereto. After a further 2 hours stirring, one dilutes with ether and extracts with 1N KOH, as well as with water. The organic phase is dried and evaporated to dryness in a vacuum. The residue is chromatographed over silica gel (elution agent: CHCl$_3$).

$R_F=0.66$, CHCl$_3$/acetone 9/1
ID$_{50}=4.6\times10^{-6}$

EXAMPLE 5

3-Dimethylamino-4-mercapto-5-mercaptomethylene-1-methylpyrrolin-2-one disodium salt of the structural formula

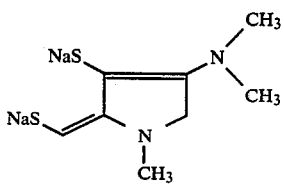

N,N-Dimethylpyrrothine reduction:

214 mg. (1 mmol) N,N-dimethylpyrrothine are suspended in 100 ml. water and mixed with 76 mg. (2 mmol) NaBH$_4$. One stirs until a clear solution is formed. The product can be purified chromatographically (silica gel) under an atmophere of nitrogen.

$R_F=0.65$, CHCl$_3$/CH$_3$OH 1/1
ID$_{50}=5\times10^{-5}$

What is claimed is:

1. A method for the inhibition of allergen-induced degranulation of peripheral leukocytes comprising administering an effective amount of a pyrrothine derivative of the formula I

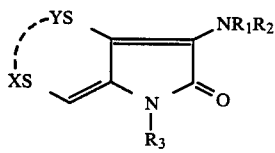

wherein R$_1$ is hydrogen or methyl, R$_2$ is hydrogen, methyl or an acyl group with 1 to 5 carbon atoms, R$_3$ is hydrogen or methyl and X and Y are hydrogen, an equivalent of a physiologically acceptable cation or together form a single bond.

2. The method of claim 1, wherein R$_1$ is hydrogen, R$_2$ is methyl or acyl with 1 to 5 carbon atoms and R$_3$ is methyl.

3. The method of claim 1 wherein the compound has formula Ia

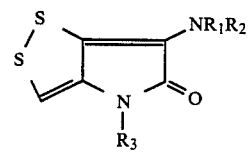

4. The method of claim 1 wherein the pyrrothine derivative is obtained from Streptoverticillium thioluteum (DSM No. 40027) or its culture broth.

5. A pyrrothine derivative compound of the formula I

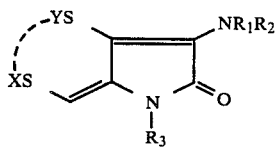

wherein R$_1$, R$_2$ and R$_3$ are methyl and X and Y are hydrogen, an equivalent of a physiologically acceptable cation or together form a single bond.

6. A pharmaceutical composition for combating allergies, containing an effective amount of the compound or mixture of compounds according to claim 5, in a pharmaceutically acceptable carrier.

7. A pharmaceutical composition for combating allergies containing an effective amount of a compound of formula I

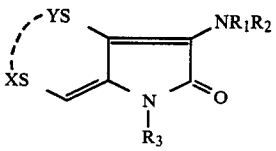

wherein R$_1$ is hydrogen or methyl, R$_2$ is hydrogen, methyl or an acyl group with 1 to 5 carbon atoms, R$_3$ is hydrogen or methyl and X and Y are hydrogen, an equivalent of a physiologically acceptable cation or together form a single bond, in a pharmaceutically acceptable carrier.

8. The method of claim 2 wherein R$_2$ is acyl with 2 to 4 carbon atoms.

9. The method of claim 2 wherein the compound has the formula Ia.

10. The method of claim 1 wherein X and Y are hydrogen, Ca$^{++}$, Na$^+$, K$^+$ or mono-, di-, or trimethylammonium ion.

* * * * *

UNITED STATES PATENT AND TRADEMARK OFFICE
CERTIFICATE OF CORRECTION

PATENT NO. : 4,760,077
DATED : July 26, 1988
INVENTOR(S) : Stahl et al.

It is certified that error appears in the above-identified patent and that said Letters Patent is hereby corrected as shown below:

Col. 4, line 22: delete "25 to 56" and insert -- 24 to 56 --.

Col. 5, line 12: delete "phyrrothine" and insert -- pyrrothine --.

Signed and Sealed this

Fourteenth Day of March, 1989

Attest:

DONALD J. QUIGG

*Attesting Officer*  *Commissioner of Patents and Trademarks*